US012337086B2

(12) United States Patent
Sternby (10) Patent No.: US 12,337,086 B2
(45) Date of Patent: Jun. 24, 2025

(54) APPARATUS AND METHOD FOR CONTROLLING INFUSION RATE OF PRE- AND POST-DILUTION IN EXTRACORPOREAL BLOOD TREATMENT (71) Applicant: GAMBRO LUNDIA AB, Lund (SE)

(72) Inventor: Jan Sternby, Lund (SE)

(73) Assignee: Gambro Lundia AB, Lund (SE)

( * ) Notice: Subject to any disclaimer, the term of this patent is extended or adjusted under 35 U.S.C. 154(b) by 713 days.

(21) Appl. No.: 17/614,016

(22) PCT Filed: Jun. 16, 2020

(86) PCT No.: PCT/EP2020/066534
§ 371 (c)(1),
(2) Date: Nov. 24, 2021

(87) PCT Pub. No.: WO2020/254269
PCT Pub. Date: Dec. 24, 2020

(65) Prior Publication Data
US 2022/0323659 A1 Oct. 13, 2022

(30) Foreign Application Priority Data
Jun. 19, 2019 (SE) .................... 1950756-5

(51) Int. Cl.
A61M 1/16 (2006.01)
A61M 1/34 (2006.01)
(52) U.S. Cl.
CPC ........ A61M 1/1615 (2014.02); A61M 1/3434 (2014.02); A61M 2202/0021 (2013.01); A61M 2205/3334 (2013.01); A61M 2210/12 (2013.01)

(58) Field of Classification Search
CPC .............. A61M 1/1615; A61M 1/3434; A61M 2202/0021; A61M 2205/3334; A61M 2210/12; A61M 1/3441
See application file for complete search history.

(56) References Cited

U.S. PATENT DOCUMENTS 8,105,260 B2 * 1/2012 Tonelli ................ A61M 1/1647
604/4.01
9,533,087 B2 1/2017 Suffritti et al.
2005/0251086 A1 11/2005 Sternby

FOREIGN PATENT DOCUMENTS

EP 0330892 B1 7/1994
EP 0547025 B1 6/1996
(Continued)

OTHER PUBLICATIONS

Pedrini et al., "Mixed-Dilution Hemodiafiltration", Hemodiafiltration: Contributions to Nephrology (2007), vol. 158, pp. 123-130.
(Continued)

Primary Examiner — Thuan D Dang
(74) Attorney, Agent, or Firm — K&L GATES LLP (57) ABSTRACT An apparatus (1a) for extracorporeal blood treatment, comprising an infusion control arrangement (8) arranged for infusing a pre-dilution flow rate upstream a blood treatment unit (4) and a post-dilution flow rate downstream the blood treatment unit (4), an ultrafiltration, UF, arrangement (40) arranged for ultrafiltration of a liquid through a semipermeable membrane (7) of the blood treatment unit (4) and a control unit (31). The control unit (31) is configured to configure the infusion control arrangement (8) to obtain a plurality of different configurations of the pre-dilution flow rate and/or post-dilution flow rate. For each of the plurality of different configurations, the control unit (31) is configured to change an operating situation of the UF arrangement (40), to detect a plurality of ultrafiltration flow rate values through (Continued)

the membrane (7) as a function of TMP, on changing said operating situation, and to evaluate an optimal ultrafiltration flow rate value from a comparison of the detected ultrafiltration flow rates. The apparatus (1a) is also configured to estimate a clearance value for a certain solute at the optimal ultrafiltration flow rate value and to evaluate a preferred configuration of the pre-dilution flow rate and/or post-dilution flow rate from a comparison of the corresponding estimated clearance values.

14 Claims, 2 Drawing Sheets

(56) References Cited

FOREIGN PATENT DOCUMENTS

| | | |
|---|---|---|
| EP | 1729836 B1 | 11/2011 |
| EP | 1773427 B1 | 1/2014 |
| WO | 2005061026 A2 | 7/2005 |
| WO | 2019002065 A1 | 1/2019 |

OTHER PUBLICATIONS

International Search Report from corresponding International Patent Application No. PCT/EP2020/066534, mailed Sep. 29, 2020.
Written Opinion of the International Searching Authority from corresponding International Patent Application No. PCT/EP2020/066534, mailed Sep. 29, 2020.

* cited by examiner

APPARATUS AND METHOD FOR CONTROLLING INFUSION RATE OF PRE- AND POST-DILUTION IN EXTRACORPOREAL BLOOD TREATMENT

PRIORITY CLAIM

The present application is a National Phase of International Application No. PCT/EP2020/066534, filed Jun. 16, 2020, which claims priority to SE Application No. 1950756-5, filed Jun. 19, 2019. The entire contents of each application are incorporated herein by reference and relied upon.

TECHNICAL FIELD

The present invention relates to the field of extracorporeal treatment of blood, and in particular apparatuses and methods that makes use of both pre- and post-infusion, i.e. infusion upstream and downstream of a blood treatment unit, respectively.

BACKGROUND

Extracorporeal treatments of blood generally involve removing blood from a patient, treating the blood and reintroducing the treated blood to the patient. Treatments of the blood because of kidney failure may include addition and/or removal of solutes from the blood, and addition and/or removal of liquid, in a dialysis treatment. As well known, dialysis treatment can be done by first removing the blood from the patient and conducting it internally of a treatment unit or dialyzer in which an exchange of solutes and liquid is performed through a semi-permeable membrane.

A number of different types of dialysis treatments may be performed, for example ultrafiltration (UF) treatment, hemofiltration (HF) treatment, hemodialysis (HD) treatment and hemodiafiltration (HDF) treatment. In UF, undesirable matter is removed from the blood by convection across the membrane into a fluid compartment. In HF treatment, undesirable matter is removed by convection and desirable matter is added to the blood, typically by dispensing a fluid into the blood either before it passes through the treatment unit and/or before it is returned to the patient. In HD treatment, a secondary fluid containing desirable matter is introduced into the fluid compartment of the treatment unit. Undesirable matter from the blood crosses the membrane into the secondary fluid and desirable matter from the secondary fluid may cross the membrane into the blood by diffusion. In HDF treatment, blood and secondary fluid exchange matter as in HD by diffusion and as in HF by convection, and, in addition, matter is added to the blood, typically by dispensing a fluid into the treated blood before it is returned to the patient.

The above described treatments enable removal of excess liquid from the patient's body. When suffering from renal failure, the patient's body collects fluid that needs to be removed during treatment. The total quantity of liquid removed during the treatment, also referred to as "total weight loss", is generally set at the start of the treatment as a target to be reached when the treatment is stopped. The total quantity is set as a quantity of liquid removed from the patient per unit time (also known as weight loss rate). The weight loss rate is for example set to a constant value or a predefined profile. It is generally desired to remove the total quantity in a short time, to minimize the treatment time. For example, document EP1773427B1 describes how to efficiently remove fluid from the patient, by monitoring the transmembrane pressure (TMP) and the ultrafiltration rate (UFR), and select the TMP that achieves the highest UFR.

Since the beginning of dialysis, efforts have been made to calculate the efficiency of the treatment mathematically. A clearance rate for a solute in the blood is a measure of the efficiency of the treatment, which depends on the characteristics of the filter used. With the membranes used in the early days it was adequate to derive a formula for clearance under the assumption of zero UF, thus only diffusive clearance. It includes the dependence of clearance on dialyzer permeability and on blood and dialysate flow rates.

The combination of convective and diffusive transport mechanisms in HDF offers the possibility to get an increased dialysis efficiency for both small and large solutes. The availability of highly permeable synthetic membranes, like polyamide, polysulfone and AN69, and of machines designed specifically for the use of these membranes, have made HDF available for clinical practice. For clearance calculations, it then becomes necessary to consider also the effect of UF on clearance. Calculating the UF effect is quite complicated, and several formulae have been proposed. It is now well known that simply adding the UF rate to the diffusive clearance will overestimate the total clearance. The reason for this is that such an addition would assume that all UF were drawn from blood having the inlet concentration of the solute. Instead, in reality, the concentration of the UF will represent a kind of average blood concentration over the length of the treatment unit.

Another effect of UF is that it changes the flow rates, and thereby also the concentration. Furthermore, UF will change the concentration profile through the membrane, which affects the local diffusion of solute.

It has been found that a combination of pre- and post-dilution allows to achieve a high clearance, as described in EP1729836. However, to control a HF or HDF treatment with both pre- and post-dilution efficiently is challenging due to the several flows and the varying concentration gradient along the membrane.

SUMMARY

It is an objective of the disclosure to alleviate at least some of the drawbacks with the prior art. It is a further objective to provide an apparatus that obtains high clearance using a combination of pre- and post-dilution. It is a further objective to provide an apparatus that obtains the high clearance efficiently, and that efficiently removes a large quantity of fluid in a relatively short time.

These objectives and others are at least partly achieved by the method and apparatus according to the independent claims and by the embodiments according to the dependent claims.

According to a first aspect, the disclosure relates to an apparatus for extracorporeal blood treatment. The apparatus comprises an infusion control arrangement arranged for infusing a pre-dilution flow rate upstream a blood treatment unit and a post-dilution flow rate downstream the blood treatment unit. The apparatus also comprises an ultrafiltration, UF, arrangement arranged for ultrafiltration of a liquid through a semipermeable membrane of a blood treatment unit, and a control unit. The control unit is configured to configure the infusion control arrangement to obtain a plurality of different configurations of the pre-dilution flow rate and/or post-dilution flow rate. For each of the plurality of different configurations, the control unit is configured to change an operating situation of the UF arrangement, detect a plurality of ultrafiltration flow rate values through the membrane as a function of TMP, on changing said operating situation and evaluate an optimal ultrafiltration flow rate value from a comparison of the detected obtained ultrafiltration flow rates. The control unit is also configured to estimate a clearance value for a certain solute at the optimal ultrafiltration flow rate value. The control unit is also configured to evaluate a preferred configuration of the pre-dilution flow rate and/or post-dilution flow rate from a comparison of the corresponding estimated clearance values.

The apparatus finds a configuration of the infusion control arrangement in simultaneous pre- and post-dilution mode, that optimizes the treatment for removing a certain solute. Thereby the benefits of having both pre-dilution and post-dilution can be obtained, at the same time as the treatment is performed as efficiently as possible.

According to a second aspect, the disclosure relates to a method for extracorporeal blood treatment in an apparatus configured to perform extracorporeal blood treatment. The method comprises configuring an infusion control arrangement arranged for infusing a pre-dilution flow rate upstream a blood treatment unit and a post-dilution flow rate downstream the blood treatment unit, to obtain a plurality of different configurations of pre-dilution flow rate and/or post-dilution flow rate. For each of the plurality of different configurations, the method comprises changing an operating situation of an ultrafiltration, UF, arrangement arranged for ultrafiltration of a liquid through a semipermeable membrane of the blood treatment unit, detecting a plurality of ultrafiltration flow rate values through the membrane as a function of TMP, on changing the operating situation, evaluating an optimal ultrafiltration flow rate value from a comparison of the detected ultrafiltration flow rates, and estimating a clearance value for a certain solute at the optimal ultrafiltration flow rate value. The method also comprises evaluating a preferred configuration of the pre-dilution flow rate and/or post-dilution flow rate from a comparison of the corresponding estimated clearance values.

According to a third aspect, the disclosure relates to a computer program comprising instructions to cause the apparatus according to the first aspect to execute the steps of the method according to the second aspect.

According to a fourth aspect, the disclosure relates to a computer-readable medium having stored thereon the computer program of the third aspect.

DETAILED DESCRIPTION

In the following disclosure, a method for extracorporeal blood treatment and an apparatus configured for performing the method will be described. With the method, a HF or HDF treatment utilizing the benefits of pre- and post-dilution may be controlled to optimize the clearance of a certain solute. The solute may be β2-microglobulin, a poisonous solute that should be removed from the blood in case the patient has become poisoned or a low molecule weight substance like urea, creatinine or phosphate.

Figure 1:
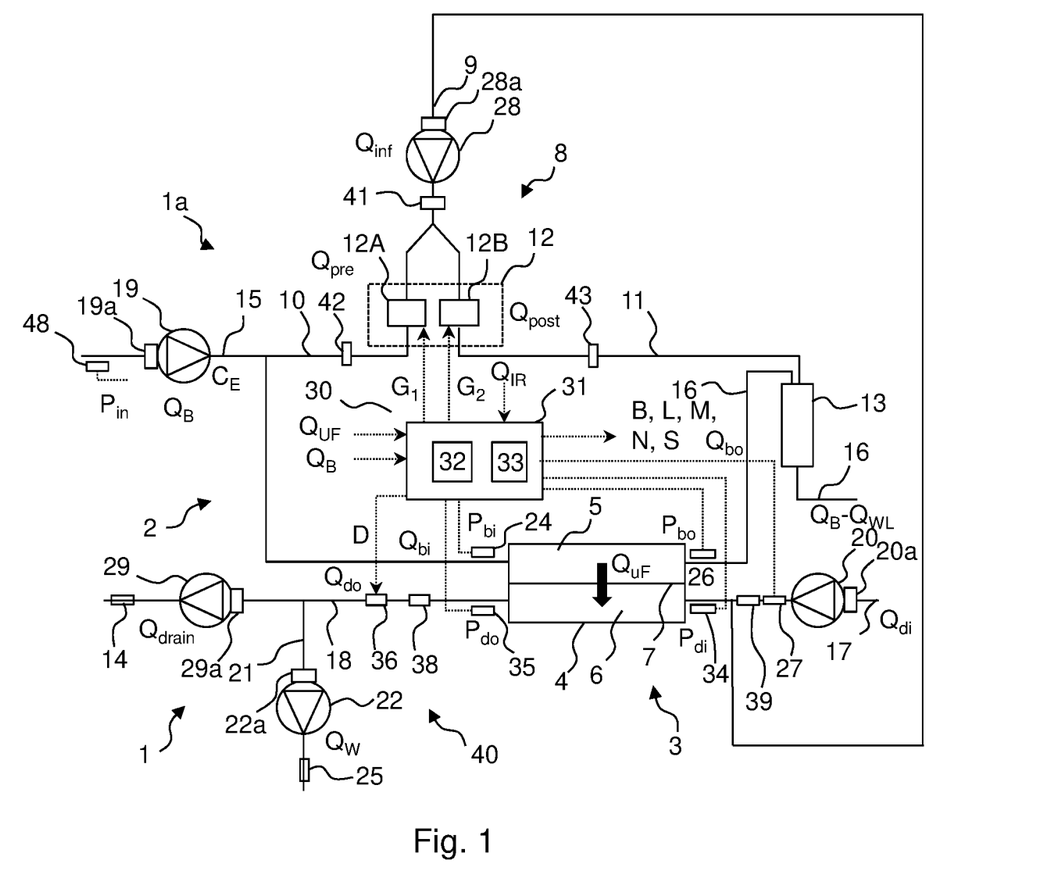
FIG. 1 illustrates a blood treatment apparatus according to some embodiments.

In FIG. 1 a renal replacement therapy system 1 is illustrated. The system 1 comprises an apparatus 1a for extracorporeal blood treatment, an extracorporeal blood circuit 2, a dialysis fluid circuit 3 and a blood treatment unit 4.

The blood treatment unit 4 may be a filter unit or a dialyzer. The blood treatment unit 4 comprises a blood compartment 5 and a fluid compartment 6 separated by a semipermeable membrane 7. The semipermeable membrane 7 is typically made of a plurality of hollow fibers.

The extracorporeal blood circuit 2 comprises an arterial line 15 connected to an inlet of the blood compartment 5, and a venous line 16 connected to an outlet of the blood compartment 5. The blood treatment unit 4 is thus arranged connected to the blood circuit 2 for extracorporeal circulation of blood. The arterial line 15 is fitted with a blood pump 19 arranged to create a blood flow rate $Q_B$ in the arterial line 15. The blood pump 19 may be a peristaltic blood pump. The venous line 16 is fitted with a drip chamber 13. The arterial line 15 may be fitted with an auxiliary drip chamber (not shown) downstream the blood pump 19. A motor (not shown) is arranged to rotate the blood pump 19. Further, the blood flow rate $Q_B$ in the arterial line downstream the blood pump 19 is mainly proportional to the blood pump speed. The blood pump speed is for example measured with a sensor 19a configured to measure the speed $\omega$ of the blood pump 19. The sensor 19a is for example a magnetic encoder. The arterial pressure $P_{in}$ is measured with a pressure sensor 48 arranged to the arterial line 15 upstream the blood pump 19.

The apparatus 1a comprises an ultrafiltration, UF, arrangement 40 arranged for ultrafiltration of a liquid through a semipermeable membrane 7 of the blood treatment unit 4. The UF arrangement 40 comprises a fresh dialysis fluid pump 20, an ultrafiltration pump 22, a drain pump 29 and an infusion control arrangement 8. In some embodiments, the UF arrangement does not include an ultrafiltration pump 22.

The dialysis fluid circuit 3 comprises a supply line 17 and a drain line 18. The supply line 17 is connected to an inlet of the fluid compartment 6, and the drain line 18 is connected to an outlet of the fluid compartment 6. The supply line 17 is fitted with the fresh dialysis fluid pump 20 arranged to create a fresh dialysis fluid flow rate $Q_{di}$. The drain line 18 is fitted with the drain pump 29 arranged to create a used fluid flow rate $Q_{drain}$. In use, the upstream end of the supply line 17 is connected to a source of fresh dialysis fluid (not shown). The downstream end of the drain line 18 is connected to a container (not shown) for accumulation of the used dialysis fluid or to a sink (not shown).

A supplemental line 21 is connected to the drain line 18 between the blood treatment unit 4 and the drain pump 29, and is fitted with the ultrafiltration pump 22 arranged to supply a desired weight loss rate, $Q_{WL}$. The ultrafiltration pump 22 is arranged to cause ultrafiltration of plasma water through the membrane 7 of the blood treatment unit 4 with an ultrafiltration rate $Q_{uF}$. When treatment is ongoing, the drain pump 29 may pump with the same flow rate as the fresh dialysis fluid pump 20. $Q_{di}$ is then equal to $Q_{drain}$, and the ultrafiltration rate $Q_{uF}$ is equal to the weight loss rate $Q_{WL}$.

The drain line 18 is fitted with a drain flow restriction device 36 for controlling a fluid flow in the drain line 18. The drain flow restriction device 36 may be arranged downstream the blood treatment unit 4, but upstream any supplemental line 21. The drain flow restriction device 36 may be a valve set, e.g. an electromechanically actuated valve set. The drain line 18 is further fitted with a sensor 14 for measuring the flow rate $Q_{drain}$ in the drain line 18 downstream the drain pump 29. The supplemental line 21 is fitted with a sensor 25 for measuring the flow rate $Q_W$ in the supplemental line 21. The sensors 14, 25 comprises for example flowmeters for measuring the fluid flow rates. The supply line 17 is further fitted with a sensor 27 for measuring a flow rate value $Q_{di}$ of the dialysis fluid pumped by the fresh dialysis fluid pump. A flow rate sensor 14, 25, 27 may be any flow meter of known type, such as a gravimetric, magnetic, ultra-sound, Coriolis effect, turbine etc.) suitable for measuring a flow rate in the lines 18, 21, 17. Alternatively, the flow rate $Q_{drain}$ is measured with a sensor 29a configured to measure the speed ω of the drain pump 29, as the liquid flow rate in the drain line 18 downstream the connection point to the supplemental line 21 is mainly proportional to the drain pump speed. The flow rate $Q_W$ may be measured with a sensor 22a configured to measure the speed ω of the ultrafiltration pump 22, as the liquid flow rate in the supplemental line 21 is mainly proportional to the ultrafiltration pump speed. Also, the flow rate $Q_{di}$ may be measured with a sensor 20a configured to measure the speed ω of the fresh dialysis fluid pump 20, as the liquid flow rate in the supply line 17 is mainly proportional to the fresh dialysis fluid pump speed. The sensors 20a, 22a, 29a are for example magnetic encoders.

The apparatus 1a also comprises an infusion control arrangement 8 arranged for infusing a pre-dilution flow rate upstream the blood treatment unit 4 and a post-dilution flow rate downstream the blood treatment unit 4. The infusion control arrangement 8 comprises an infusion pump 28 and a flow control means 12. In an alternative embodiment, the infusion control arrangement 8 instead of one infusion pump 28 comprises two infusion pumps, whereof one pre-dilution pump arranged to supply a pre-dilution flow rate and one post-dilution pump arranged to supply a post-dilution flow rate (not shown).

The infusion control arrangement 8 is connected to the extracorporeal blood circuit 2 by means of fluid lines. The infusion control arrangement 8 comprises a main line 9, which forks into a pre-dilution line 10 and a post-dilution line 11 at one end. At the other end, the main line 9 is connected to the supply line 17, e.g. downstream the fresh dialysis fluid pump 20. The infusion control arrangement 8 thus withdraws its substitution fluid from the fresh dialysis fluid, in FIG. 1 from the supply line 17. In an alternative embodiment not illustrated, the infusion control arrangement 8 withdraws its substitution fluid from another source of substitution fluid The pre-dilution line 10 is connected to the arterial line 15, e.g. downstream the blood pump 19, and upstream the blood treatment unit 4. The post-dilution line 11 is connected to the venous line 16, and here the post-dilution line 11 is connected to the venous drip chamber 13 in the venous line 16. However, alternative connections of the post-dilution line 11 to the to the venous line 16 are possible. The pre-dilution line 10 is thus arranged for infusion of substitution fluid upstream the treatment unit 4. Further, the post-dilution line 11 is arranged for infusion of substitution fluid downstream the treatment unit 4. The main line 9 is fitted with the infusion pump 28 supplying a flow rate $Q_{IR}$. A flow rate sensor 41 is arranged to measure the flow rate of the substitution fluid pumped by the infusion pump 28. The flow control means 12 is arranged to regulate a pre-dilution flow rate $Q_{pre}$ of substitution fluid in the pre-dilution line 10 and a post-dilution flow rate of substitution fluid in the post-dilution line 11. The flow control means 12 may comprise a first flow restriction device 12A arranged to the pre-dilution line 10, and a second flow restriction device 12B arranged to the post-dilution line 11. The first and second flow restriction devices 12A and 12B may be independently controlled. Thus, the first flow restriction device 12A is arranged to regulate a flow rate $Q_{pre}$ in the pre-dilution line 10, and the second flow restriction device 12B is arranged to regulate a flow rate $Q_{post}$ in the post-dilution line 11. The flow restriction devices 12A, 12B may be valve sets, such as electromechanically actuated valve sets. One or both of the flow restriction devices 12A, 12B may instead be a pump or pumps (not shown) arranged to the pre-dilution line 10 and the post-dilution line 11, respectively. If both the flow restriction devices 12A, 12B are pumps (the first flow restriction device 12A includes a first pump, and the second restriction device 12B includes a second pump), the infusion pump 28 may be removed. In some embodiments, a first flow rate sensor 42 is arranged to measure the flow rate $Q_{pre}$ in the pre-dilution line 10. Thereby the flow rate $Q_{pre}$ in the pre-dilution line 10 may be monitored. In some embodiments, a second flow rate sensor 43 is arranged to measure the flow rate $Q_{post}$ in the post-dilution line 11. Thereby the flow rate $Q_{post}$ in the post-dilution line 10 may be monitored. In an alternative embodiment, the flow control means 12 may comprise a common flow restriction device (not shown) fitted to the pre-dilution line 10 and the post-dilution line 11.

The flow rate of the dialysis fluid at the inlet of the fluid compartment 6 is the flow rate of the dialysis fluid $Q_{di}$ minus the flow rate of the substitution fluid $Q_{inf}$.

In an alternative embodiment, the ultrafiltration pump 22, the supplemental line 21 and the sensor 25 are removed. The flow rate $Q_{drain}$ of the drain pump 29 is then increased to also withdraw the WL amount (thus $Q_{WL}$). The flow rate $Q_{drain}$ then $Q_{di}$ plus $Q_{WL}$.

The apparatus 1a further comprises a control circuit 30 comprising a control unit 31. The control unit 31 comprises a processor 32 and a memory 33. The control unit 31 is configured to control the apparatus 1a, i.e. the pumps, the valves etc, according to control instructions.

In use, the flow rate of substitution fluid is regulated by adjusting the delivery, by the infusion pump 28, of the substitution fluid. The control unit 31 is configured to generate a control signal L to regulate the flow rate $Q_{IR}$ of fluid generated by the infusion pump 28. The settings of the flow restriction devices 12A and 12B thereafter determines how the flow should be partitioned conducted in the pre-dilution line 10 or in the post-dilution line 11. The control unit 31 may be configured to generate a control signal $G_1$ to regulate the first flow restriction device 12A, and to generate a control signal $G_2$ to regulate the second flow restriction device 12B. Alternatively, if the flow restriction devices 12A and 12B are two infusion pumps, these pumps are configured to provide the respective flow.

The dialysis fluid and the substitution fluid are thus the same kind of fluids, and comes from the same source. The fluids may be electrolyte and/or buffer solutions. The substitution fluid may also be referred to as infusion fluid or replacement fluid.

Although not illustrated in the FIG. 1, the renal replacement therapy system 1 may comprise at least one system for preparation of the dialysis fluid comprising arrangement for e.g. mixing the fluid. This may be referred to as on-line preparation of the dialysis fluid. In the following disclosure, on-line preparation of the used fluids is assumed.

The system 1 may be set in a plurality of different modes to automatically enable different kinds of treatments, for example hemofiltration (HF) or hemodiafiltration (HDF). Because of the flow control means 12 and the infusion pump 28, it is possible to switch between post-dilution mode, pre-dilution mode and simultaneous post-dilution and pre-dilution mode, without manual intervention, and also during treatment.

The total quantity of liquid removed during the treatment, referred to as "total weight loss", is typically set at the start of the treatment as a target to be reached when the treatment is stopped. The time duration of the treatment may be referred to as the "total treatment time" and is also typically set at the start of the treatment. The quantity of liquid removed from the patient may be set per unit of time, also known as the Weight Loss Rate, WLR. The WLR may be set to a constant value or to a predetermined profile, and is generally referred to herein as $Q_{WL}$.

The ultrafiltration rate $Q_{uF}$ is the rate of removal of fluid (i.e. ultrafiltrate) from the blood, filtered through the membrane 7. The ultrafiltration rate $Q_{uF}$ is equal to $Q_{drain}+Q_W-(Q_{di}-Q_{inf})$. Typically, $Q_{drain}$ is regulated such that it is equal to $Q_{di}$, and then $Q_{uF}$ is equal to $Q_W$ (which shall be equal to $Q_{WL}$) plus $Q_{inf}$. Alternatively, if $Q_W=0$, then $Q_{drain}=Q_{di}+Q_{WL}$. The patient weight loss rate $Q_{WL}$ is equal to the difference between the ultrafiltration rate $Q_{uF}$ through the membrane 7 and the flow rate $Q_{inf}$ of the substitution fluid. In other words, the patient weight loss rate $Q_{wL}$ is equal to $Q_{uF}-Q_{inf}$.

In case of HF, there is no added dialysis fluid flow at the inlet of the dialysis chamber 6, but there is a substitution fluid flow rate $Q_{inf}$ to the blood. $Q_{di}$ is then used as the substitution fluid flow rate $Q_{inf}$. The ultrafiltration flow rate $Q_{uF}$ is then equal to the used dialysis fluid rate ($Q_{drain}+Q_W$), while the patient weight loss rate $Q_{WL}=Q_{uF}-Q_{inf}=(Q_{drain}+Q_W)-Q_{inf}$. Alternatively, the part of the flow $Q_{di}$ that is not used as substitution fluid flow rate $Q_{inf}$, is bypassed the blood treatment unit 4.

In case of HDF, there is both a dialysis fluid flow at the inlet of the dialysis chamber 6, thus $Q_{di}-Q_{inf}$, and a substitution fluid flow rate $Q_{inf}$. The ultrafiltration flow rate $Q_{uF}$ is then equal to the used dialysis fluid rate ($Q_{drain}+Q_W$) minus the fresh dialysis fluid rate into the fluid chamber 6 ($Q_{di}-Q_{inf}$), while the patient weight loss rate $Q_{WL}=Q_{uF}-Q_{inf}=(Q_{drain}+Q_W)-(Q_{di}-Q_{inf})-Q_{inf}=(Q_{drain}+Q_W)-Q_{di}$. In one embodiment, $Q_{di}$ and $Q_{drain}$ are balanced to be equal, and $Q_W$ controlled such that $Q_W$ is equal to the desired weight loss rate. Thus, in the embodiment shown in FIG. 1, the WLR is set by the ultrafiltration pump 22, and the actual WLR is measured by the sensor 25 or 22a as $Q_W$.

In case the system 1 has on-line preparation of substitution fluid, the total ultrafiltration (UF) across the membrane 7 may be controlled in at least two ways by the ultrafiltration pump 22 (or the drain pump 29 if there is no separate ultrafiltration pump 22) and the infusion pump 28; in volume mode and in TMP mode. In both modes, the difference between the flow rates $Q_{di}-Q_W$ and $Q_{drain}$ used to control the ultrafiltration pump 22 and the drain pump 29 such that the difference agrees with the desired weight loss rate. If no ultrafiltration pump 22 and fluid line 21 are present, the drain pump 29 withdraws also the $Q_{WL}$ amount, and the difference between the flow rates $Q_{di}$ and $Q_{drain}$ is used to control the drain pump 29 such that the difference agrees with the desired weight loss rate. In volume mode, the infusion pump 28 is kept at a constant flow rate $Q_{inf}$, and the TMP is allowed to vary, as needed to get the desired weight loss rate. In TMP mode the desired TMP is maintained constant by controlling the infusion flow rate $Q_{inf}$ of the infusion pump 28. The relation $Q_{WL}=Q_{uF}-Q_{inf}$ is maintained in both modes. The control unit 31 is configured to control the system 1 to either volume mode or TMP mode.

The control unit 31 is programmed to cause the apparatus 1a to perform a certain procedure. An aim of the procedure is to determine a configuration of the apparatus 1a that gives an optimal clearance for a certain solute. The procedure may be performed before or during a treatment. An optimal clearance is for example the best clearance (value) for the certain solute, thus, the clearance that withdraws the greatest amount of the certain solute. The procedure is intended for HF and HDF, using mixed pre- and post-dilution. Use of mixed pre- and post-dilution may also be referred to as mixed dilution, or simultaneous pre- and post-dilution. To obtain mixed pre- and post-dilution, the pre- and post-dilution flow rates for example are set as independent flow rates or as a ratio of pre-dilution flow rate to post-dilution flow rate. In the apparatus 1a in FIG. 1, the infusion control arrangement 8 is configured to obtain different configurations. For example, the total infusion flow rate is configured by regulating the infusion pump 28. The distribution between pre-dilution flow and post-dilution flow is configured by regulating the flow control means 12.

Initially, an initial pre-dilution flow rate, an initial post-dilution flow rate and/or a desired Weight Loss volume and/or a total treatment time and/or an initial ratio of pre-dilution flow rate to post-dilution flow rate may be set to the apparatus 1a. The initial values of the flow rates and ratio, and the desired Weight Loss volume may be determined by a medical doctor's prescription or determined by a user of the apparatus 1a. The flow rates and the ratio are configured by configuring the infusion control arrangement 8. The configuring may be performed manually e.g. by input from an operator to a user interface (not shown) of the apparatus 1, or performed automatically by the control unit 31 (e.g. using saved or remotely obtained values or corresponding data).

The control unit 31 is configured to evaluate a plurality of different configurations of the infusion control arrangement, by performing a procedure for each different configuration to evaluate the best UF-flow rate, estimate the clearance for that UF-flow rate, and to find the best clearance among the plurality of different configurations. This procedure may be referred to as a TMP-scanning, as the procedure includes to find the optimum TMP. In order to evaluate the different configurations, the control unit 31 is configured to configure the infusion control arrangement 8 to obtain a plurality of different configurations of pre-dilution flow rate and/or post-dilution flow rate. A configuration of the infusion control arrangement 8 implies a pre-dilution flow rate and a post-dilution flow rate that each is greater than zero. To configure the infusion control arrangement 8 may include to change the pre-dilution flow rate, or to change the ratio of the pre-dilution flow rate to the post-dilution flow rate. In some embodiments, to configure the infusion control arrangement also comprises to change the post-dilution flow rate. The configurations have mutually different flow rates or ratios.

In one embodiment, the plurality of different configurations comprises different pre-dilution flow rates. For example, the pre-dilution flow rate is changed to a value different from any other used value during the process, and is not allowed to vary before it is configured to a new pre-dilution flow rate. The value of the post-dilution flow rate is not initially changed, but during the TMP-scanning the post-dilution flow rate may change as a result of the optimization. The different pre-dilution flow rates may be a predetermined set of flow rates, or may be a set of flow rates that are determined during execution of the procedure. For example, the pre-dilution flow rate is a function of the blood flow rate $Q_B$. The pre-dilution flow rate is typically set in an interval from 5% to 100% of the blood flow rate $Q_B$. For example, the pre-dilution flow rate is between 20 ml/min to 400 ml/min, if the blood flow rate $Q_B$ is 400 ml/min.

In another embodiment, the plurality of different configurations comprises different ratios of pre-dilution flow rate to post-dilution flow rate. For example, 1:1, 1:2, 1:3, 2:1, 3:1 etc. The pre-dilution flow rate and the post-dilution flow rate may then have any value as specified above, as long as the selected ratio is maintained. During each TMP-scanning (explained below) the selected ratio is maintained. The pre- and post-dilution flow rates are thus allowed to vary during the optimization but only to the extent that the present selected ratio is maintained.

For each configuration of the plurality of configurations, the control unit 31 is configured to perform the abovementioned procedure, that is, a TMP scanning. A purpose of the scanning is to optimize the efficiency of the ultrafiltration for the selected configuration of the infusion control arrangement 8.

The procedure comprises to increase or decrease the TMP in steps, to find the maximum UF-rate point. The TMP is changed, by means of the control unit 31, by changing an operating situation of the UF arrangement 40. To change an operating situation includes to change a property of the UF arrangement 40. In one embodiment, the control unit 31 is configured to change the operating situation of the UF arrangement 40 by increasing and/or decreasing the speed of the infusion pump 28. The speed of the infusion pump 28 is for example increased or decreased in steps. When the speed of the infusion pump 28 is changed, this affects the dialysis fluid flow into the fluid compartment 6 according to $Q_{di}-Q_{inf}$. The drain pump $Q_{drain}$ is configured to withdraw the same amount of fluid flow that enters the fluid compartment 6, and its speed is then changed such that it provides a fluid flow rate that is equal to $Q_{di}-Q_{inf}$. The speed of the ultrafiltration pump 22 is not changed. As a result, the TMP is changed. The TMP is calculated on the basis of pressure values measured at the inlets and outlets of the blood treatment unit 4. Upon a change of the speed of the infusion pump 28, the post-dilution flow rate and the pre-dilution flow rate are changed accordingly, while maintaining the present configuration of pre-dilution flow rate, or ratio of pre-dilution flow rate to post-dilution flow rate. If the present configuration includes a constant pre-dilution flow rate, then when the speed of the infusion pump 28 is changed, it will only affect the post-dilution flow rate. If the present configuration includes a constant ratio of pre-dilution flow rate to post-dilution flow rate, then when the speed of the infusion pump 28 is changed, it will affect both flows, but to the extent that the ratio is maintained. Thus, both flows will be proportionally changed. Of course, if the single infusion pump 28 is exchanged for two infusion pumps, one controlling the pre-dilution flow rate and one controlling the post-dilution flow rate, these pumps are controlled in a corresponding way. Thus, if the present configuration includes a constant pre-dilution flow rate, then when the infusion rate should be changed, the speed of the post-infusion pump (not shown) is changed with the intended infusion rate change, and the speed of the pre-dilution pump (not shown) is held constant. If the present configuration includes a constant ratio of pre-dilution flow rate to post-dilution flow rate, then the speed of the pre-dilution pump and the speed of the post-dilution pump will be proportionally changed, to maintain the ratio. The control unit 31 is configured to determine or calculate how much the speed of the pump or pumps should be changed, or how much/long time the restriction devices 12A, 12B should be open, to provide the desired pre-dilution flow rate and the post-dilution flow rate. Further, the control unit 31 is configured to maintain the relation $Q_{uF}=Q_{WL}+Q_{inf}$ (i.e. $Q_{WL}=Q_{uF}-Q_{inf}$). In other words, the control unit 31 is configured to adjust the post-dilution flow rate, and in some embodiments also the pre-dilution flow rate, in correspondence to the ultrafiltration flow rate in accordance with: ultrafiltration flow rate=Weight Loss rate+pre-dilution flow rate+post-dilution flow rate.

The procedure further comprises, by means of the control unit 31, to detect a plurality of ultrafiltration flow rate values $Q_{uF}$ through the membrane 7 as a function of TMP, on changing the operating situation. The plurality of ultrafiltration flow rate values $Q_{uF}$ comprises at least two values of the ultrafiltration flow rate $Q_{uF}$ that are detected, in two different operating situations of the UF arrangement 40. Thus, a change of the operating situation of the UF arrangement 40 changes the operating situations from at least a first operating situation to a second operating situation. Thus, a first value of the ultrafiltration rate is detected at a first operating situation of the UF arrangement, and a second value of the ultrafiltration rate is detected at a second operating situation of the UF arrangement 40. A change of the operating situation of the UF arrangement 40 may also affect the TMP over the membrane 7. Thus, that the ultrafiltration flow rate values are detected as a function of transmembrane pressure, TMP, means that the ultrafiltration flow rate values that are detected, are related to, or are correlated with, the TMP. Thus, if the TMP changes, the ultrafiltration flow rates will also change. The ultrafiltration flow rate $Q_{WL}$ is determined from the relation $Q_{uF}=Q_{WL}+Q_{inf}$.

The procedure further comprises, by means of the control unit 31, to evaluate an optimal ultrafiltration flow rate value from a comparison of the detected ultrafiltration flow rates. For example, an optimal ultrafiltration flow rate being the maximum ultrafiltration flow rate of the detected ultrafiltration flow rates is determined.

In one embodiment, the control unit 31 is configured to detect, in two different operating situations of the UF arrangement 40, at least two values of the ultrafiltration flow rate and at least two values of a quantity indicative of an operating situation of the UF arrangement 40 (for example the TMP or a speed of the infusion pump 28, or the speeds of a first infusion pump and a second infusion pumps, if present). An optimal ultrafiltration flow rate is then determined by a subsequent control whether the values satisfy or not a predetermined relation with a reference value. For example, a change in the ultrafiltration flow rate $\Delta Q_{uF}$ and a change in the transmembrane pressure $\Delta TMP$ are determined, by effect of the above-mentioned change, and checking if $\Delta Q_{uF}/\Delta TMP \le \varphi$, where $\varphi$ is a constant value close to zero. If $\Delta Q_{uF}/\Delta TMP > \varphi$, the control unit 31 repeats the described operations for a different TMP value. If $\Delta Q_{uF}/\Delta TMP \le \varphi$, the control unit 31 does not repeat the operations, the control unit 31 evaluates an optimal ultrafiltration flow rate of the obtained flow rates. As the ultrafiltration flow rate is a function of TMP, the optimal ultrafiltration flow rate corresponds to an optimal value of the TMP. The configuration of the UF arrangement 40 at the optimal ultrafiltration flow rate and the optimal TMP are saved, such that the control unit 31 later can control the UF arrangement 31 to obtain the optimal ultrafiltration flow rate at the optimal TMP. Generally, when there is more or less no increase of the ultrafiltration flow rate upon increasing the TMP, then it is of no use to increase the TMP more.

In another embodiment, the control unit 31 is configured to determine a derivative of the ultrafiltration rate, as a function of a quantity indicative of an operating situation of the UF arrangement 40 (for example TMP or a speed of the infusion pump 28). An optimal ultrafiltration flow rate is then determined by a subsequent control whether the derivative satisfy or not a predetermined relation with a limit reference value. Other alternatives can be found in the patent EP1773427B1.

The optimal ultrafiltration flow rate is thus the ultrafiltration flow rate $Q_{uF}$ that as a function of TMP has a maximum or, has a derivative that assumes a null or positive value which is smaller than a small limit value.

When an optimal ultrafiltration flow rate has been found for a configuration of the plurality of configurations of the infusion control arrangement 40, the control unit 31 is configured to estimate a clearance value for a certain solute at the optimal ultrafiltration flow rate value. The certain solute is for example β2-microglobulin, a poisonous substance, or, in case of HF-treatment, a low molecule weight substance such as urea, creatinine or phosphate. The clearance value may be calculated by means of equation (1), compensated with equation (3) that will be described in the following. In the estimation of the clearance value for the certain solute, the control unit 31 may thus include a dilution factor that depends on the pre-dilution flow rate. For urea, the clearance value may alternatively be determined by measuring conductivity on the dialysate side of the blood treatment unit 4 at the optimal ultrafiltration flow rate, and from these measurements calculate the clearance. This procedure is for example performed with a "Diascan Monitoring System" from Baxter, see e.g. EP0330892B1 and EP0547025B1 for more information.

The estimation procedure is performed for each of the different configurations of the infusion control arrangement 40, and will thus result in a plurality of clearance values.

The control unit 31 is configured to evaluate a preferred configuration of the pre-dilution flow rate and/or ratio from a comparison of the corresponding estimated clearance values. For example, the configuration that gives the maximum clearance for a certain solute is determined as a preferred configuration. Thus, the preferred configuration is a ratio or pre-dilution flow rate value corresponding to an estimated clearance value being at least one of equal to, in relation to, and proximal to a maximum value of the values of the estimated clearance values.

The clearance of a certain solute may be estimated in a plurality of ways. Urea is for example assumed to be distributed both inside and outside of the cells, that is in blood water, whereas β2-microglobulin is only present in plasma water. This has the effect that the flow rate that should be used in the clearance calculation differs between different solutes.

When ultrafiltration takes place it increases the solute transport by adding a convective part. Another effect of ultrafiltration is that it changes the concentration profile across the membrane 7, and this will affect the diffusive force. For the derivation of a clearance formula, it is therefore needed to study separately the solute transport across the membrane 7 at a given point along the treatment unit 4. This can be done assuming a constant ultrafiltration per unit length. It is also assumed that there is a distribution of pore sizes in the membrane 4 so that larger solutes may only pass the larger pores. The result is that for larger solutes the concentration in the ultrafiltrate may be smaller than the concentration on the blood side. This is quantified by Staverman's reflection coefficient σ which defines the percentage of molecules in the ultrafiltrate that is stopped by the membrane.

The solute concentrations at any given point along the treatment unit 4 may be calculated by setting up a mass balance for each of the two compartments 5, 6 of the treatment unit 4. With the assumptions above and a transport across the membrane 7 that is the amount of a diffusional term that is proportional to the concentration difference and a convective term, this will lead to two coupled differential equations for the solute concentrations along the treatment unit 4. The coefficients of the resulting differential equations will vary along the treatment unit 4 according to the flow rates, but can still be solved analytically with the following result for clearance:

$$K_b = \frac{Q_{bi}Q_{di} - f \cdot (Q_{bi} - Q_u) \cdot (Q_B + Q_{uF})}{Q_{di} - f \cdot (Q_{bi} - Q_{uF})} \qquad (1)$$

where $$f = \left[\frac{Q_{bo}}{Q_{bi}} \cdot \frac{Q_{do}}{Q_{di}}\right]^{k_0 A \cdot \gamma / Q_{uF}} \text{ with } \gamma = \frac{Q_{uF}}{k_0 A \cdot \left(e^{Q_{uF}/k_0 A} - 1\right)} \qquad (2)$$

and where $k_o A$ is the mass transfer area coefficient which specifies the permeability of a membrane with area A for a certain solute, $Q_{bi}$ and $Q_{di}$ are the inlet blood and dialysis fluid flow rates to the treatment unit 4, $Q_{bo}$ and $Q_{do}$ the two outlet flows and $Q_{uF}$ is the ultrafiltration rate. Note that this formula is valid also in the case of backfiltration ($Q_{uF}$<0). As understood, $Q_{bi}$ is equal to $Q_B+Q_{pre}$ and $Q_{bo}$ is equal to $Q_{bi}-Q_{uF}$. Thus, each solute has a $k_o$-value that is specific for that solute. Thus, the $k_o$-value is different for different solutes.

When using pre-dilution, the clearance calculated in equation (1) should be multiplied with a dilution factor:

$$\text{dilution factor} = \frac{Q_{bw}}{Q_{bw} + Q_{pre}} \qquad (3)$$

where $Q_{bw}$ is the blood water flow rate. The blood water flow rate $Q_{bw}$ may be estimated from:

$$Q_{bw} = (0.73 \cdot Hct + (1-Hct) + (1-0.00107 \cdot C_p)) \cdot Q_b \qquad (4)$$

where Hct is the fraction of red blood cells in the blood (a value between 0-1, typically 0.25-0.45), $C_p$ is the total amount of protein in the blood in g/L. $Q_{bw}$ may be estimated from predetermined values of Hct and $C_p$, for example Hct is 0.30 or 0.35, and $C_p$ is 70 g/L. The value 0.73 is the fraction of water internally in red blood cells. The value 0.00107 multiplied with $C_p$ tells the amount of protein in the plasma volume. The control unit 31 may thus be programmed to calculate the clearance value for the certain solute by using a dilution factor that depends on the pre-dilution flow rate.

The certain solute is for example β2-microglobulin. The certain solute may alternatively be a toxin such as a toxic alkaloid, for example muscarine, agaricine or phalline. In case of HF-treatment, the certain solute may be a low molecule weight substance such as urea, creatinine or phosphate.

The clearance may alternatively be estimated from measurements of conductivity of the used dialysis fluid or measurement of concentration of a solute in the used dialysis fluid, e.g. in the drain line 18, by a sensor 38 arranged to measure a property of the used dialysis fluid indicative of the conductivity or concentration of the solute. The sensor 38 is e.g. a temperature compensated conductivity cell. A further sensor 39 arranged to the dialysate inlet line 17, is the same type of sensor as the sensor 38, and is arranged to sense the same type of fluid parameter. The sensor or sensors 38, 39 may be calibrated to a certain solute, and thus to detect conductivity or concentration of the certain solute. The control unit 31 is connected to the sensor or sensors 38, 39 for receiving signals or data relating to values of the fluid parameter. From the values the control unit 31 is configured to calculate or estimate a clearance value for the certain solute. For example, the control unit 31 is configured to calculate a difference between the detected properties indicative of conductivity or concentration on the dialysate fluid and the used dialysis fluid, and from the difference estimate a clearance value of the certain solute. Thus, the control unit 31 is configured to estimate the clearance value from a difference in conductivity between an incoming flow of fresh dialysis fluid to the blood treatment unit 4, and an outgoing flow of used dialysis fluid from the blood treatment unit 4.

When a clearance value for each configuration has been determined, the configuration giving the greatest clearance is determined by comparing the clearance values with each other. The result may be presented to the user of the apparatus 1a, such that the user self manually can configure the apparatus 1a to obtain the configuration of the infusion arrangement 8 and the TMP that gave the most optimal, i.e. the greatest clearance for the certain solute. Alternatively, the apparatus 1a is automatically configured to obtain the configurations to achieve the optimal clearance for the certain solute.

Apart from the sensors and valves already described, the control circuit 30 comprises a sensor 24 arranged to the arterial line 15 directly upstream of the blood treatment unit 4 for measuring a pressure value $P_{bi}$ correlated to the blood pressure at the inlet of the blood treatment unit 4. The control circuit 30 further comprises a sensor 26 arranged to the venous line 16 directly downstream from the blood treatment unit 4 for measuring a pressure value $P_{bo}$ correlated to the blood pressure at the outlet of the blood treatment unit 4. The control circuit 30 further comprises a sensor 34 arranged to the supply line 17 for measuring a pressure value $P_{di}$ correlated to the dialysis fluid pressure at the inlet of the blood treatment unit 4. The control circuit 30 further comprises a sensor 35 arranged to the drain line 18 for measuring a pressure value $P_{do}$ correlated to the dialysis fluid pressure at the outlet of the blood treatment unit 4. The control circuit 30 may further comprise a sensor (not shown) arranged to the drain line 18 for measuring a flow rate value correlated to the flow rate of the dialysis fluid at the outlet of the blood treatment unit 4 (and upstream any supplemental line 21). It should be understood that the described apparatus 1a is merely an example, and the apparatus 1a may not comprise all of the above described sensors. Hence, the apparatus 1a may alternatively comprise more or less, and/or others than the described sensors.

The system may further comprise at least one heater arranged to heat the dialysis fluid and/or the substitution fluid and at least one degassing unit for degassing the dialysis fluid and/or the substitution fluid. The renal replacement therapy system 1 may also comprise various monitoring means comprising sensors, and optionally alarms, for detecting leakage anywhere in the system 1, for detecting abnormal behavior, for monitoring of various parameters such as conductivity, temperature, density, pH and other blood parameters, fluid parameters and/or system parameters.

One or several of the configured and/or measured values are communicated to the control unit 31 as signals or data from the sensors etc. The control unit 31 is configured to receive the signals or data and is configured to calculate e.g. the TMP, the clearance K, the UF coefficient, the UFR and other parameters using the received values based on control instructions. The TMP may be expressed as a difference in pressure between the blood pressure in the blood compartment 5 and the fluid pressure in the fluid compartment 6. The TMP may thus be determined by calculating the difference between the blood pressure in the blood chamber 5 and the pressure in the fluid chamber 6. The blood pressure in the blood chamber 5 may be determined by $P_{bo}$ or $P_{bi}$, or an average of $P_{bi}$ and $P_{bo}$. The fluid pressure in the fluid chamber 6 may be determined by $P_{do}$ or $P_{di}$, or an average of $P_{do}$ or $P_{di}$. The TMP may be calculated as a difference between any of the $P_{bo}$, $P_{bi}$ or average of ($P_{bi}$ and $P_{bo}$), and any of the $P_{do}$, $P_{di}$ or average of ($P_{di}$ and $P_{do}$). For example, the TMP may be calculated as a difference between the post-filter pressures $P_{bo}$ and $P_{do}$. Alternatively, the TMP is calculated as a difference between an average value of the blood pressure in the blood compartment 5 i.e. $P_{bi}$ and $P_{bo}$; and $P_{do}$ downstream the fluid compartment 6 (the post-filter fluid pressure). As a further alternative, the TMP is calculated as a difference between an average value of the blood pressure in the blood compartment 5 i.e. $P_{bi}$ and $P_{bo}$, and an average value of the fluid pressure in the fluid compartment 6, i.e. $P_{di}$ and $P_{do}$. In practice, the control unit 31 emits output signals for controlling the flow control means 12, e.g. the restriction devices 12A and 12B, the infusion pump 28 and in some embodiments the fresh dialysis fluid pump 20, the drain pump 29, the ultrafiltration pump 22 and the blood pump 19, according to control instructions as will be made clear in the following description. For example, the control unit 31 may be configured to generate a control signal M for regulating the fresh dialysis fluid flow rate $Q_{di}$, and a control signal N for regulating the used fluid flow rate $Q_{drain}$. Further, the control unit 31 may be configured to generate a control signal S for regulating the flow rate $Q_W$ generated by the ultrafiltration pump 22. The control unit 31 may also be configured to generate a control signal B for regulating the blood flow rate $Q_B$, and other control signals for regulating the infusion flow rates $Q_{inf}$, $Q_{pre}$, $Q_{post}$.

The disclosure also relates to a method for extracorporeal blood treatment in an apparatus configured to perform extracorporeal blood treatment, e.g. the apparatus 1a described in FIG. 1. The method may be saved as computer instructions on a computer readable medium in the control unit 30 of the apparatus 1a, whereby the computer instructions are executed by a processor 32 of the control unit 30. The method will now be explained with reference to the flow chart in FIG. 2. Before the method is started, the method may include configuring S0 an initial pre-dilution flow rate, an initial post-dilution flow rate and/or a desired Weight Loss volume and/or a total treatment time and/or an initial ratio of pre-dilution flow rate to post-dilution flow rate.

The method comprises configuring S10 an infusion control arrangement 8 arranged for infusing a pre-dilution flow rate upstream a blood treatment unit 4 and a post-dilution flow rate downstream the blood treatment unit 4, to obtain a plurality of different configurations of pre-dilution flow rate and/or post-dilution flow rate. For each of the plurality of different configurations, the method comprises changing S11a an operating situation of an ultrafiltration, UF, arrangement 40 arranged for ultrafiltration of a liquid through a semipermeable membrane 7 of the blood treatment unit 4, detecting S11b a plurality of ultrafiltration flow rate values through the membrane 7 as a function of TMP, on changing the operating situation and evaluating S11c an optimal ultrafiltration flow rate value from a comparison of the detected ultrafiltration flow rates. Thus, for each of the plurality of configurations of the arrangement for UF 8, the method comprises determining an optimal ultrafiltration flow rate. The steps S11a-S11c may be referred to as a TMP-scanning, commonly referred to in FIG. 2 as step S11. The method also comprises estimating S12 a clearance value for a certain solute at the optimal ultrafiltration flow rate value. In other words, for each optimal ultrafiltration flow rate value, the method comprises estimating a clearance value for the certain solute. In some embodiments, the estimating S12 comprises including a dilution factor that depends on the pre-dilution flow rate in the estimation of the clearance value for the certain solute. In a step S10a, the method checks if all the plurality of different configurations has been evaluated. If no, the method returns to step S11a. If yes, the method continues to step S13.

Figure 2:
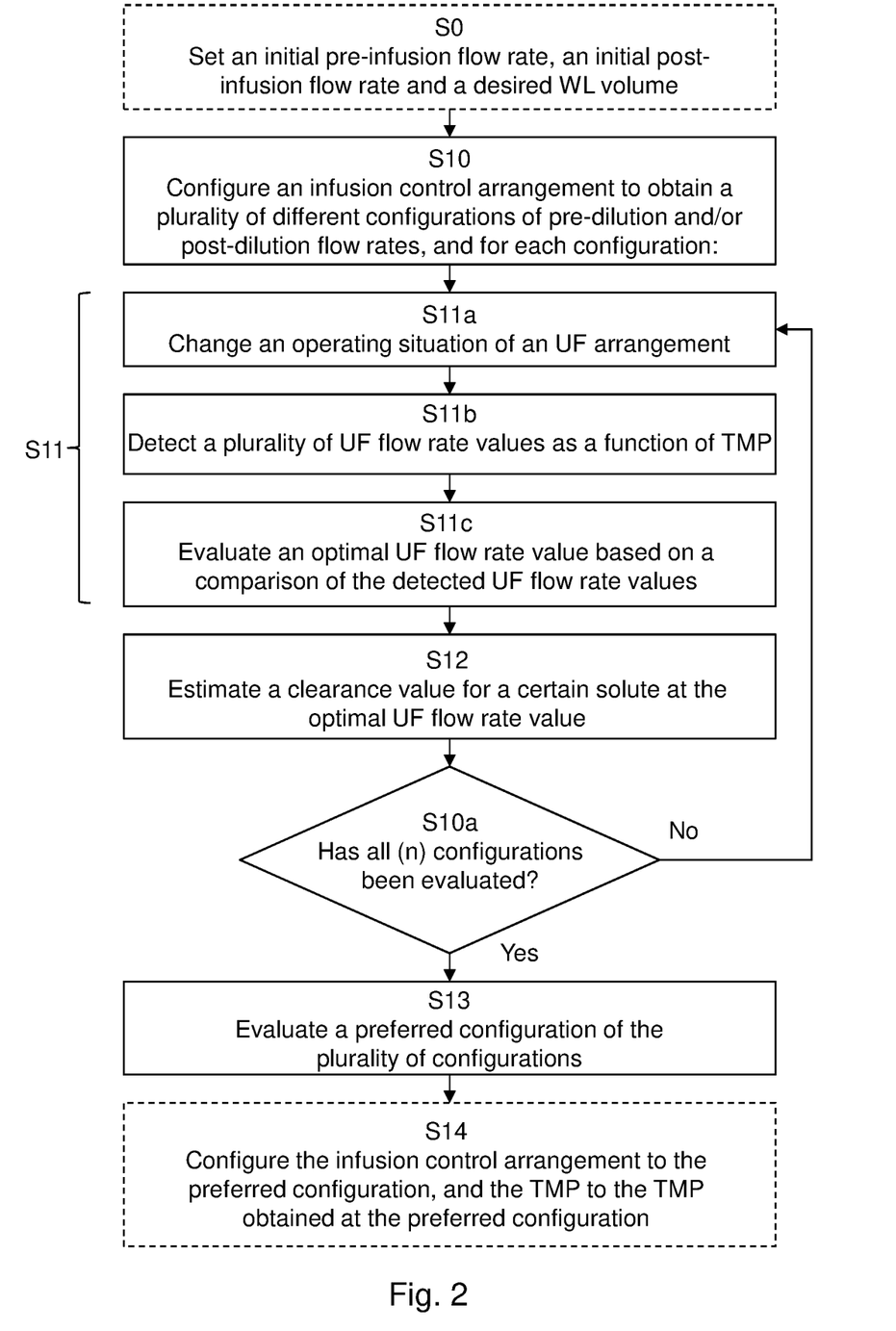
FIG. 2 illustrates a method for extracorporeal blood treatment according to some embodiments.

In step S13, the method comprises evaluating S13 a preferred configuration of the pre-dilution flow rate and/or post-dilution flow rate from a comparison of the corresponding estimated clearance values. For example, the evaluating S13 comprises evaluating a preferred configuration being a ratio or pre-dilution flow rate value corresponding to an estimated clearance value being at least one of equal to, in relation to, and proximal to a maximum value of the values of the estimated clearance values. Typically, the method comprises estimating an optimal clearance value being the maximum value of the values. The configuration giving the optimal clearance value is selected as the preferred configuration. The method may also include the step S14 of configuring the infusion control arrangement to the preferred configuration, and the TMP to the TMP obtained at the preferred configuration. The configuration may be set automatically by the control unit 31, or manually by means of the operator.

Example

An example of a HF or HDF apparatus will now be described. The apparatus prepares dialysis fluid on-line, and the dialysis fluid is partitioned into a substitution fluid flow with a flow rate $Q_{inf}$ and a fresh dialysis fluid flow with a flow rate $Q_{di}$–$Q_{inf}$. The apparatus is for example the apparatus illustrated in FIG. 1.

Before the treatment is started, the operator initiates a process to find the best distribution of the substitution fluid flow (the distribution between pre-dilution and post-dilution) to provide an optimal clearance of a certain solute. The certain solute is for example obtained from a prescription of a doctor. The operator for example presses a start-button on a touch screen of the apparatus, which starts the process. The process can be fully automatic; thus, no operator input is needed.

The operator sets a prescribed Weight Loss volume to be removed during treatment. The operator also sets an infusion volume or a total treatment time. The operator may also set an initial TMP, an initial pre-dilution flow rate, an initial post-dilution flow rate and/or an initial ratio of pre-dilution flow rate to post-dilution flow rate.

By pressing the start-button, the apparatus will start the procedure for finding the optimal clearance for the certain solute. The pre-dilution flow rate or the ratio of pre-dilution flow rate to the post-dilution flow rate, is changed according to a predefined pattern. For example, the ratio of pre-dilution flow rate to post-dilution flow rate is changed in steps. Alternatively, the pre-dilution flow rate is changed in steps, and the post-dilution flow rate will thereby be changed automatically such that the relation $Q_{WL}=Q_{uF}-Q_{inf}$ is maintained. The pattern may include 2-10 different configurations of the infusion control arrangement, e.g. 2-10 different ratios or 2-20 different pre-dilution flow rates. A step change may comprise between 5-20 ml/min change, e.g. 5, 10, 15 or 20 ml/min change of the pre-dilution flow rate from the previous value of the pre-dilution flow rate.

For each configuration, a TMP-scan is performed where the TMP is changed in steps (increased or decreased) to find the maximum UF-rate point. This corresponds to step S11 in FIG. 2. The TMP is changed by changing an operating situation of the arrangement for UF. The TMP-scan starts at the initial set TMP. Alternatively, the scan will start with a short period in volume control mode, in order to get a stable TMP start value. An optimal UF-rate is determined for each configuration. Hence, the total substitution rate $Q_{inf}$ is optimized for each ratio.

The apparatus then determines a clearance value for the certain solute for the optimal UF-rate of each configuration (corresponding to step S12), and finally selects the maximum clearance value amongst the determined clearance values (corresponding to step S13). The maximum clearance value is presented to the operator as optimal. The operator may accept or not the optimal clearance value.

If accepted, the configuration of the apparatus to achieve the optimal clearance may be automatically set, thus the TMP, the configuration of the infusion arrangement etc. (corresponding to step S14). The configuration of the apparatus to achieve the optimal clearance value may also be presented to the operator, such as the TMP, the configuration of the infusion arrangement and the configuration of the arrangement for UF.

Alternatively, the operator may set the configurations of the apparatus manually to achieve the optimal clearance according to the displayed TMP, the configuration of the infusion arrangement and the configuration of the arrangement for UF.

This procedure is preferably performed at the beginning of the treatment, but may also be performed at regular times during treatment.

While the invention has been described in connection with what are presently considered to be the most practical and preferred embodiments, it is to be understood that the invention is not to be limited to the disclosed embodiments, but on the contrary, is intended to cover various modifications and equivalent arrangements included within the spirit and the scope of the appended claims.

The invention claimed is:
1. An apparatus for an extracorporeal blood treatment, the apparatus comprising:
   an infusion control arrangement arranged for infusing a substitution fluid at a pre-dilution flow rate upstream of a blood treatment unit and infusing the substitution fluid at a post-dilution flow rate downstream from the blood treatment unit;
   an ultrafiltration arrangement arranged for ultrafiltration of a liquid through a semipermeable membrane of the blood treatment unit; and
   a control unit configured to:
      configure the infusion control arrangement to obtain a plurality of different configurations of the pre-dilu- tion flow rate and/or the post-dilution flow rate, and for each of the plurality of different configurations:
change an operating situation of the ultrafiltration arrangement,
detect a plurality of ultrafiltration flow rate values through the membrane as a function of transmembrane pressure upon changing said operating situation,
determine an optimal ultrafiltration flow rate value from a comparison of the detected plurality of ultrafiltration flow rate values, and
estimate a clearance value for a solute at the optimal ultrafiltration flow rate value, and
determine a preferred configuration of the pre-dilution flow rate and/or the post-dilution flow rate from a comparison of the estimated clearance values for each of the plurality of different configurations.

2. The apparatus according to claim 1, wherein the plurality of different configurations comprises different ratios of the pre-dilution flow rate to the post-dilution flow rate, or different pre-dilution flow rates.

3. The apparatus according to claim 1, wherein the preferred configuration includes a ratio or a pre-dilution flow rate value corresponding to an estimated clearance value being equal to or related to a maximum value of the estimated clearance values.

4. The apparatus according to claim 1, wherein the control unit is further configured to configure an initial pre-dilution flow rate, an initial post-dilution flow rate, a total treatment time, a desired weight loss volume, and/or an initial ratio of the pre-dilution flow rate to the post-dilution flow rate.

5. The apparatus according to claim 1, wherein the control unit is configured to include a dilution factor that depends on the pre-dilution flow rate, in the estimation of the clearance value for the solute.

6. The apparatus according to claim 1, wherein the control unit is configured to estimate the clearance value from a difference in conductivity between an incoming flow of fresh dialysis fluid to the ultrafiltration arrangement and an outgoing flow of used dialysis fluid from the ultrafiltration arrangement.

7. The apparatus according to claim 1, wherein the solute is β2-microglobulin, urea, creatinine, or phosphate.

8. A method for an extracorporeal blood treatment in an apparatus configured to perform the extracorporeal blood treatment, the method comprising:
configuring an infusion control arrangement so as to obtain a plurality of different configurations of a pre-dilution flow rate of a substitution fluid and/or a post-dilution flow rate of the substitution fluid, the infusion control arrangement arranged for infusing the substitution fluid at the pre-dilution flow rate upstream of a blood treatment unit and a post-dilution flow rate downstream of the blood treatment unit, and for each of the plurality of different configurations:
changing an operating situation of an ultrafiltration arrangement arranged for ultrafiltration of a liquid through a semipermeable membrane of the blood treatment unit;
detecting a plurality of ultrafiltration flow rate values through the membrane as a function of transmembrane pressure upon changing said operating situation;
determining an optimal ultrafiltration flow rate value from a comparison of the detected ultrafiltration flow rate values; and
estimating a clearance value for a solute at the optimal ultrafiltration flow rate value; and
determining a preferred configuration of the pre-dilution flow rate and/or the post-dilution flow rate from a comparison of the estimated clearance values for each of the plurality of different configurations.

9. The method according to claim 8, wherein the plurality of different configurations comprises different ratios of the pre-dilution flow rate to the post-dilution flow rate, or different pre-dilution flow rates.

10. The method according to claim 8, wherein determining the preferred configuration includes determining the preferred configuration to be a ratio or a pre-dilution flow rate value corresponding to an estimated clearance value being equal to or related to a maximum value of the estimated clearance values.

11. The method according to claim 8, wherein the estimating comprises including a dilution factor that depends on the pre-dilution flow rate in the estimation of the clearance value for the solute.

12. The method according to claim 8, further comprising configuring an initial pre-dilution flow rate, an initial post-dilution flow rate, a desired weight loss volume, a total treatment time, and/or an initial ratio of the pre-dilution flow rate to the post-dilution flow rate.

13. The method according to claim 8, wherein the solute is β2-microglobulin, urea, creatinine, or phosphate.

14. A non-transitory, computer-readable medium storing instructions, which when executed by a processor, cause the processor to:
configure an infusion control arrangement to obtain a plurality of different configurations of a pre-dilution flow rate and/or a post-dilution flow rate, the infusion control arrangement arranged for infusing a substitution fluid at a pre-dilution flow rate upstream of a blood treatment unit and infusing the substitution fluid at a post-dilution flow rate downstream from the blood treatment unit, and for each of the plurality of different configurations:
change an operating situation of an ultrafiltration arrangement, the ultrafiltration arrangement arranged for ultrafiltration of a liquid through a semipermeable membrane of the blood treatment unit,
detect a plurality of ultrafiltration flow rate values through the membrane as a function of transmembrane pressure upon changing said operating situation,
determine an optimal ultrafiltration flow rate value from a comparison of the detected plurality of ultrafiltration flow rate values, and
estimate a clearance value for a solute at the optimal ultrafiltration flow rate value, and
determine a preferred configuration of the pre-dilution flow rate and/or the post-dilution flow rate from a comparison of the estimated clearance values for each of the plurality of different configurations.

* * * * *